(12) United States Patent
Cohen et al.

(10) Patent No.: US 8,253,936 B2
(45) Date of Patent: Aug. 28, 2012

(54) RAMAN CHARACTERIZATION OF TRANSPLANT TISSUE

(75) Inventors: Jeffrey Cohen, Pittsburgh, PA (US); John S Maier, Pittsburgh, PA (US); Shona Stewart, Pittsburgh, PA (US)

(73) Assignee: ChemImage Corporation, Pittsburgh, PA (US)

( * ) Notice: Subject to any disclaimer, the term of this patent is extended or adjusted under 35 U.S.C. 154(b) by 445 days.

(21) Appl. No.: 12/537,513

(22) Filed: Aug. 7, 2009

(65) Prior Publication Data

US 2010/0034743 A1  Feb. 11, 2010

Related U.S. Application Data

(60) Provisional application No. 61/087,345, filed on Aug. 8, 2008.

(51) Int. Cl.
G01J 3/44 (2006.01)
(52) U.S. Cl. .......................................... 356/301
(58) Field of Classification Search .................. 356/301
See application file for complete search history.

(56) References Cited

U.S. PATENT DOCUMENTS

| | | | |
|---|---|---|---|
| 4,080,073 A | 3/1978 | Wolga |
| 4,564,761 A | 1/1986 | Buckwald |
| 4,696,896 A | 9/1987 | Brinton |
| 5,004,681 A | 4/1991 | Boyse |
| 5,239,169 A | 8/1993 | Thomas |
| 5,539,517 A | 7/1996 | Cabib |
| 5,580,714 A | 12/1996 | Polovina |
| 5,687,730 A | 11/1997 | Doiron |
| 5,784,162 A | 7/1998 | Cabib |
| 5,866,430 A | 2/1999 | Grow |
| 5,919,135 A | 7/1999 | Lemelson |
| 5,991,653 A | 11/1999 | Richards-Kortum |
| 6,002,476 A | 12/1999 | Treado |
| 6,040,906 A | 3/2000 | Harhay |
| 6,070,583 A | 6/2000 | Perelman |
| 6,091,985 A | 7/2000 | Alfano |
| 6,174,291 B1 | 1/2001 | McMahon |
| 6,201,989 B1 | 3/2001 | Whitehead |
| 6,205,354 B1 | 3/2001 | Gellermann |

(Continued)

FOREIGN PATENT DOCUMENTS

CA   2007048225   5/2007

(Continued)

OTHER PUBLICATIONS

Chung et al, Detection of Heart Transplant Rejection Using Raman Spectroscopy, School of Biomedical Engineering, Science and Health Systems, Drexel University, Showcase, 2006.*

(Continued)

*Primary Examiner* — Kara E Geisel

(57) ABSTRACT

A system and method for determining a disease state and clinical outcome of a sample. A sample is illuminated to produce Raman scattered photons, the Raman scattered photons are assessed to generate a Raman spectroscopic data set representative of the sample, wherein said Raman spectroscopic data set comprises at least one of: a Raman spectra of the sample and a spatially accurate wavelength resolved Raman image of the sample; the Raman spectroscopic data set is evaluated using a chemometric technique to classify the disease state of the sample as: acute, chronic, incipient, or none. In one embodiment, the chemontric technique is principle component analysis. In another embodiment, the sample is obtained prior to transplantation and analysis can determine the likelihood of rejection by a host.

18 Claims, 11 Drawing Sheets

U.S. PATENT DOCUMENTS

| | | |
|---|---|---|
| 6,283,236 B1 | 9/2001 | Teal et al. |
| 6,424,859 B2 | 7/2002 | Jackson |
| 6,449,087 B2 | 9/2002 | Ogino |
| 6,485,413 B1 | 11/2002 | Boppart |
| 6,586,246 B1 | 7/2003 | Yoon |
| 6,642,012 B1 | 11/2003 | Ashdown |
| 6,681,133 B2 | 1/2004 | Chaiken |
| 6,697,665 B1 | 2/2004 | Rava |
| 6,788,965 B2 | 9/2004 | Ruchti |
| 6,826,422 B1 | 11/2004 | Modell |
| 6,950,184 B2 | 9/2005 | Stewart |
| 7,515,952 B2 | 4/2009 | Balas |
| 7,697,576 B2 | 4/2010 | Maier |
| 2001/0044129 A1 | 11/2001 | Ling |
| 2003/0018272 A1 | 1/2003 | Treado |
| 2003/0133105 A1 | 7/2003 | Gorelik et al. |
| 2003/0143580 A1 | 7/2003 | Straus |
| 2003/0191398 A1 | 10/2003 | Motz |
| 2004/0010197 A1 | 1/2004 | Faupel |
| 2004/0033514 A1 | 2/2004 | Rothschild |
| 2004/0207625 A1 | 10/2004 | Griffin |
| 2005/0052645 A1 | 3/2005 | Stewart |
| 2005/0250091 A1 | 11/2005 | Maier |
| 2005/0277816 A1 | 12/2005 | Maier |
| 2006/0253261 A1 | 11/2006 | Maier |
| 2006/0281068 A1 | 12/2006 | Maier et al. |
| 2007/0070343 A1 | 3/2007 | Cohen |
| 2007/0099951 A1 | 5/2007 | Dube et al. |
| 2007/0127022 A1 | 6/2007 | Cohen |
| 2007/0178067 A1 | 8/2007 | Maier |
| 2007/0182959 A1 | 8/2007 | Maier |
| 2008/0070940 A1 | 3/2008 | Dube et al. |
| 2008/0117416 A1 | 5/2008 | Hunter et al. |
| 2008/0318247 A1 | 12/2008 | Chang et al. |

FOREIGN PATENT DOCUMENTS

| | | |
|---|---|---|
| EP | 0990134 | 10/2005 |
| JP | 09121889 | 5/1997 |
| WO | WO9303672 | 3/1993 |
| WO | WO9730338 | 6/1997 |
| WO | WO02077587 | 10/2002 |
| WO | 03060444 | 7/2003 |
| WO | WO2004051242 | 6/2004 |
| WO | 2005060380 | 7/2005 |
| WO | 2006135628 | 12/2006 |
| WO | 2008052221 | 5/2008 |
| WO | 2008014429 | 11/2008 |

OTHER PUBLICATIONS

Van De Poll, S.W.E. et al., "Atheriosclerosis, Thrombosis, and Vascular Biology," 2001, 21. 1630-1635 and supplementary information.

Leroy et al, "Canine Prostate Carcinomas Express Markers of Urogelial and Prostatic Differentiation," Vet. Pathol, (2004) 41:131-140.

Technology License Opportunity, "Hyperspectral Imaging for Cancer Detection," 2 pp (c) 2004 Science Applications International Corporation.

Miseo et al, "Developing a Chemical-Imaging Camera," The Industrial Physicist, Oct./Nov. 2003, 29-32.

Chen et al, "Proceedings of the National Science Council," ROC Part B: Life Science, 1996: 20(4): 123-130.

Huang et al, Int. J. Cancer, 2003, 107, 1047-1052.

Hawi et al, Cancer Letters 1996, 110:35-40.

Redd, D. C.B. et al, Applied Spectroscopy, 1993, 47, 787-791.

Frank et al, Analytical Chemistry 1994, 6, 319-326.

Schaeberle et al, Analytical Chemistry, 1996, 68, 1829-1833.

Kline et al., Journal of Raman Spectroscopy, 1997, 28, 119-124.

Sijtsema et al, Applied Spectroscopy, 1998, 52. 348-355.

Colarusso et al, SPIE 1999, 3608, 139-145.

Beljebbar et al, SPIE 1999, 3608, 175-184.

Morris et al, SPIE 2000, 3918, 2-8.

Nijssen et al, Journal of Investigative Dermatology, 2002, 119, 64-69.

Shafer-Peltier, K.E. et al, Journal of Cellular Biochemistry, Supplement 2002, 39, 125-137.

Koljenovis et al, Laboratory Investigation, 2002, 83. 1265-1277.

Ling et al, Applied Optics, 2002, 41. 6006-6017.

Uzunbajakava et al, Biopolymers 2003, 72. 1-9.

Uzunbajakava et al, SPIE 2003, 4963, 223-230.

Widaja et al. Appllect Spectroscopy, 2003, 57. 1353-1362.

Van Manen et al, Journal of the American Chemical Society 2003, 125, 12112-12113.

Joshi et al, SPIE 2004, 5324, 89-95.

Heinirich et al, Applied Physics Letters, 2004, 84, 816-818.

Maier et al, SPIE 2004, 5588, 98-105.

Stewart et al, "A Fast Method for Detecting Cryptosporidium Parvum Oocysts in Real World Samples," Advanced Biomedical and Clincial Diagnostic Systems III, SPIE, vol. 5692, 2005, pp. 341-350.

Maquelin et al, "Identification of Medically Relevant Microorganisms by Vibrational Spectroscopy," Journal of Microbiological Methods, Elsevier, Amsterdam, NL, vol, 51, No. 3, Nov. 1, 2002 pp. 255-271.

Extended European Search Report, PCT/US2006029187, Nov. 24, 2009.

Supplementary European Search Report, PCT/US03/00868, Oct. 8, 2010.

Written Opinion of the International Searching Authority, PCT/US2006/029187, Aug. 29, 2008.

International Preliminary Report on Patentability, PCT/US2006/029187, Mar. 1, 2011.

Brown et al., Raman Spectroscopic Differentiation of Activated Versus Non-Activated T Lymphocytes: An In Vitro Study of an Acute Allograft Rejection Model, Journal of Immunological Methods, vol. 340, Issue 1, Jan. 1 2009, pp. 48-54.

\* cited by examiner

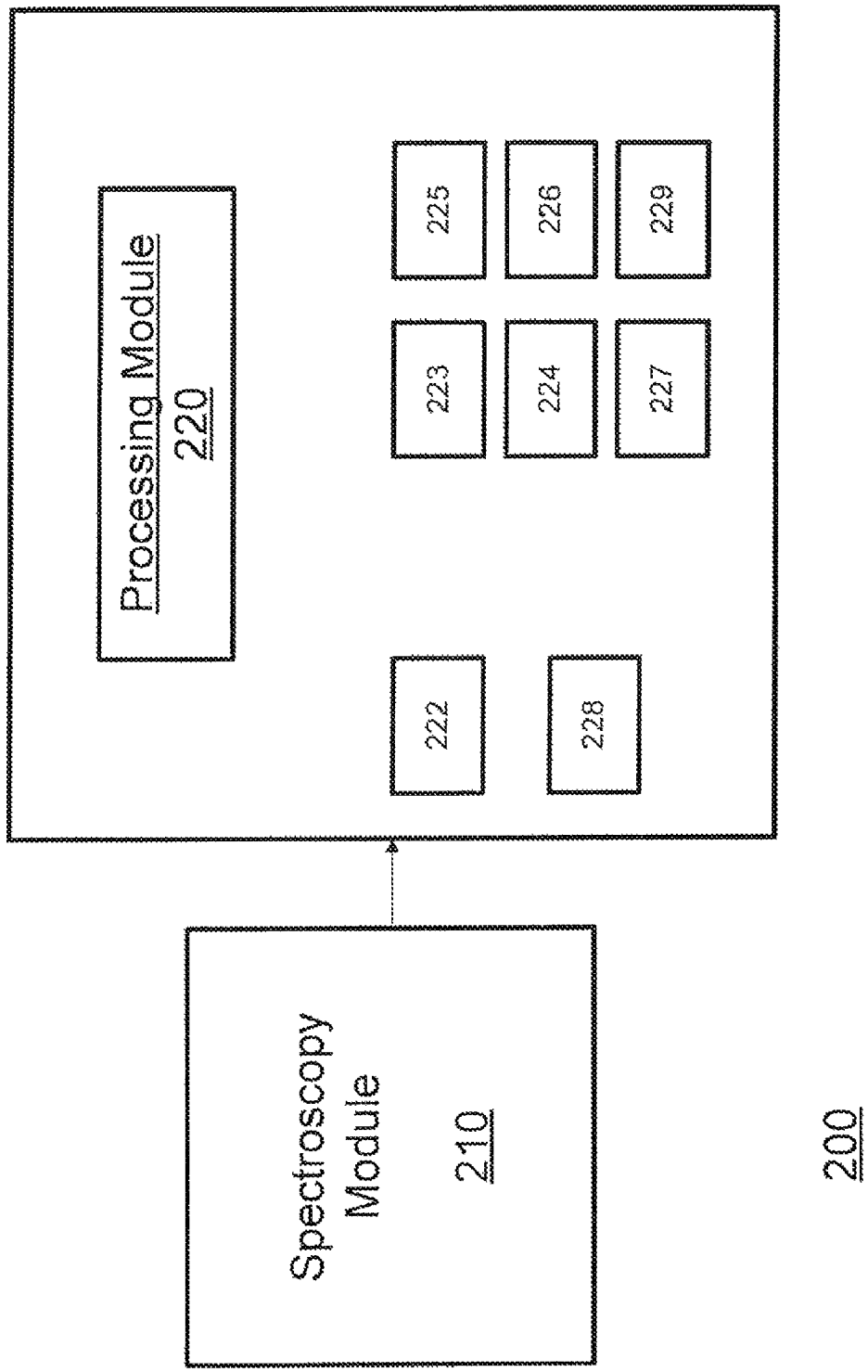

RAMAN CHARACTERIZATION OF TRANSPLANT TISSUE

RELATED APPLICATIONS

This application claims priority to U.S. Non-Provisional Application No. 61/087,345, filed on Aug. 8, 2008, entitled "Raman Characterization of Transplant Tissue".

BACKGROUND OF THE INVENTION

The biochemical composition of a cell is a complex mix of biological molecules including, but not limited to, proteins, nucleic acids, lipids, and carbohydrates. The composition and interaction of the biological molecules determines the metabolic state of a cell. The metabolic state of the cell will dictate the type of cell and its function (i.e., red blood cell, epithelial cell, etc.). Tissue is generally understood to mean a group of cells that work together to perform a function. An organ is generally understood to mean a group of tissues organized to perform a function. Raman spectroscopic techniques provide information about the biological molecules contained in cells, tissues, and organs and therefore provide information about the metabolic state. As the cell's, tissue's, or organ's metabolic state changes from the normal state to a diseased state. Raman spectroscopic techniques can provide information to indicate the metabolic change and therefore serve to diagnose and predict a disease state and a clinical outcome in a patient.

Organ transplantation is a final alternative treatment in several diseases including but not limited to kidney failure, heart failure, lung failure, liver failure, tendon and ligament failure, corneal clouding, and lens failure, among others. There are also diseases and conditions where the treatment includes transplanting bone, bone marrow, skin, hematoetic cells, or other cells.

When an organ, tissue, or other material is transplanted into a host, rejection of the material by die host is always possible. Rejection of transplanted material can occur either acutely or chronically. In the case of acute rejection, there is a relatively rapid reaction between the transplanted material and the cells and tissues of the receiving patient. In the case of chronic rejection there is a slower progression of reaction to the transplanted tissue. Both forms of rejection can occur within the context of different transplanted organs and occur by complex physiological pathways which are not completely understood.

In the specific case of kidney transplant, approximately 30% of transplanted kidneys go through a process of chronic rejection. Such rejection may occur days, weeks or months after the transplant has taken place. There is no known way to predict the development of chronic rejection in the case of a specific kidney, donor, or recipient.

Raman spectroscopy holds potential for the detection of various types of incipient or occurring rejection. Because Raman spectroscopy is based on irradiation of a sample and detection of scattered radiation, it can be employed non-invasively to analyze biological samples in situ. Thus, little or no sample preparation is required. Raman spectroscopy techniques can be readily performed in aqueous environments because water exhibits very little, but predictable, Raman scattering. It is particularly amenable to in vivo measurements as the powers and excitation wavelengths used are non-destructive to the tissue and have a relatively large penetration depth. Therefore, it is desirable to devise methodologies that use Raman spectroscopy and imaging techniques to differentiate various cell types, to classify disease states of biological samples under investigation, and to predict clinical outcomes in patients.

SUMMARY OF THE INVENTION

The systems and methods of the present disclose provide for the use of Raman scattering measurements, including Raman spectroscopy and Raman chemical imaging, to evaluate tissues identified for transplantation into a host and determine the likelihood of their rejection by a host. The systems and methods disclosed herein can also be used to analyze tissues which have been transplanted into a host to thereby determine a disease state and a clinical outcome in a patient.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

FIG. 2 is representative of a system of the present disclosure;

DETAILED DESCRIPTION

Reference will now be made in detail to the preferred embodiments of the present disclosure, examples of which are illustrated in the accompanying drawings. Wherever possible the same reference numbers will be used throughout the drawings to refer to the same or like parts.

Figure 1:
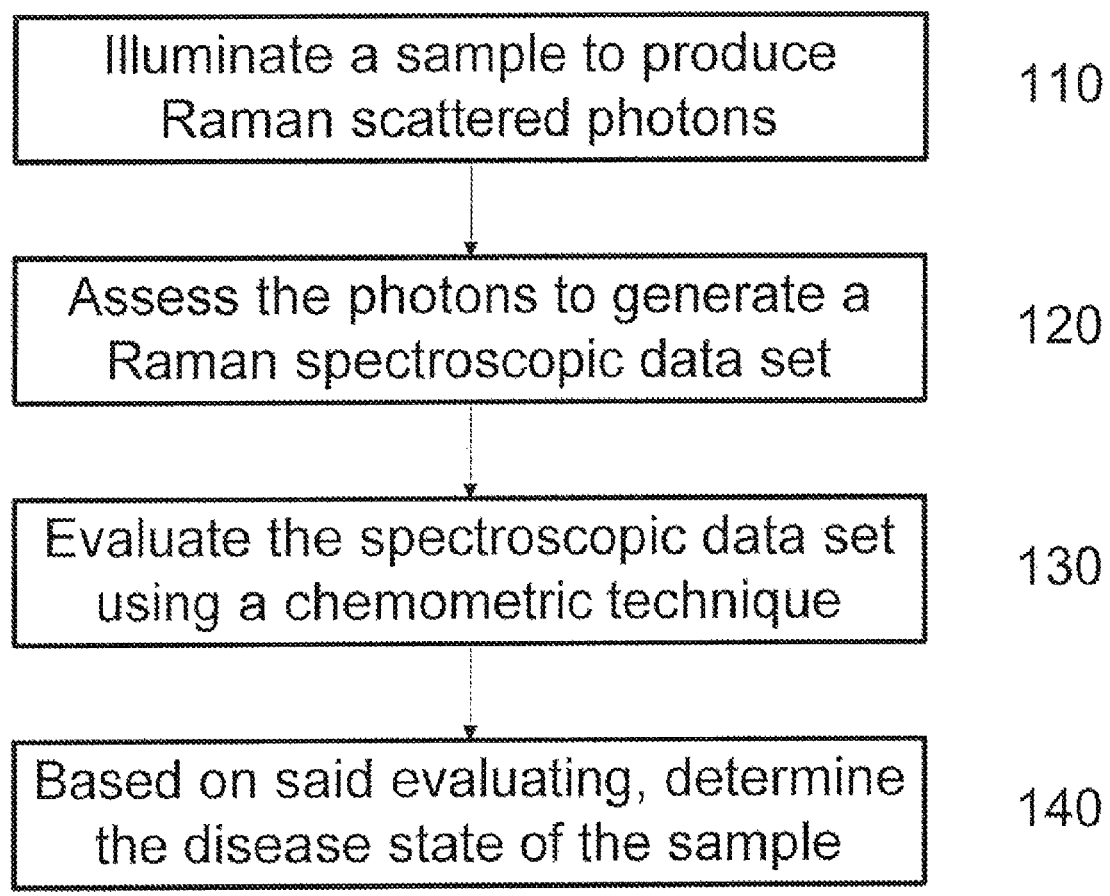
FIG. 1 is illustrative of a method of the present disclosure.

The systems and methods of the present disclosure provide for the classification of a disease state of a biological tissue sample. FIG. 1 illustrates one method of the present disclosure. The method 100 comprises illuminating a sample with substantially monochromatic light to thereby produce Raman scattered photons in step 110. The Raman scattered photons are assessed in step 120 to thereby generate a Raman spectroscopic data set representative of the sample. In one embodiment, the spectroscopic data set may include at least one of: a Raman spectra and a spatially accurate wavelength resolved Raman image. In step 130, the Raman spectroscopic data set is evaluated using a chemometric technique to thereby classify a disease state of the sample in step 140. In one embodiment, the disease state of the sample may include but is not limited to: no state of rejection, a state of acute rejection, a state of chronic rejection, and a state of incipient rejection.

The terms "sample", "unknown sample", "test sample", and "target sample" may be used interchangeably herein to refer to a biological sample under investigation, wherein such interchange use may be without reference to such biological sample's disease state or clinical outcome. In one embodiment, the sample comprises a biological tissue sample. The biological sample may be any organ, tissue, cell, extracellular material, or other biological material including but not limited to that material associated with: kidney, heart, heart valve, vein, artery, tendon, ligament, breast, pancreas, prostate, lung, liver, blood, muscle, nerve, bladder, intestine, stomach, corneal, lens, bone, bone marrow, skin, hematopoetic cells, and other types of cells including stem cells (e.g., those produced in a laboratory or clinical setting).

In another embodiment the sample may be a non-human sample, for example organ or tissue material obtained from an animal (e.g., a xenograft). In yet another embodiment, the organ or tissue under investigation may be the result of tissue engineering or other such technology.

The sample may comprise a biological tissue section removed from an organ identified for transplant into a recipient or a tissue section removed from an organ that has been transplanted into recipient. The sample can be removed from the organ using any method known in the art including but not limited to: fine needle aspiration, core biopsy, and surgical biopsy. Therefore, the whole organ is not required for analysis. In one embodiment, the sample is prepared for Raman evaluation by placing it on a slide suitable for the analysis (e.g., an aluminum coated slide). The sample may comprise cells from the organ and extracellular material from the organ. The sample may also comprise a standard tissue section with cells and extracellular material in approximately their normal orientation on the slide. In another embodiment, the sample may comprise cells of plants, non-mammalian animals, fungi, protists. and monera. The sample may also comprise, in another embodiment, an unknown sample. In such an embodiment, it is possible that the source or identity of the sample is unknown. It is also possible that the unknown sample is a biological sample under analysis to determine its metabolic state or its disease status or to determine whether the disease status will progress to another level.

The present disclosure also provides for a system for analyzing samples that can be used to diagnose a disease state and/or a clinical outcome in a patient. The system includes a reference data base, an illumination source, a spectroscopic device, a machine readable program code, and a processor. The reference data base comprises a plurality of reference spectral data sets which may be associated with one or more of: a known material, a known disease state, and a known clinical outcome. The spectral data sets may include spectra and images, including spatially accurate wavelength resolved images, including but not limited to Raman, infrared (including near infrared and mid infrared), ultraviolet, fluorescence, and visible spectroscopic data, among others. In one embodiment, the illumination source is configured to illuminate a sample with substantially monochromatic light to thereby generate scattered photons. In such an embodiment, the spectroscopic device is configured to collect a test Raman data set based on the scattered photons. The processor can be operatively coupled to the illumination source and the spectroscopic device, and configured to execute the machine readable program code so as to perform a series of steps. In one such embodiment, the spectroscopic device includes an imaging spectrometer. In another embodiment, the spectroscopic device includes a dispersive spectrometer and a fiber array spectral translator.

A schematic layout of one system of the present disclosure is provided in FIG. 2. FIG. 2 illustrates an exemplary system 200 according to one embodiment of the present disclosure. System 200 includes a spectroscopy module 210 in communication with a processing module 220. Processing module 220 may include a processor 222, data bases 223, 224, 225 and 226, and machine readable program code 228. In one embodiment, 229 can be a Raman data base. In another embodiment, 229 can be another data base. The machine readable program code 228 may contain executable program instructions, and the processor 222 may be configured to execute the machine readable program code 228 so as to perform the methods of the present disclosure. In one embodiment, the program code 228 may contain the ChemImage Xpert™ software marketed by ChemImage Corporation of Pittsburgh, Pa. The ChemImage Xpert™ software may be used to process spectroscopic data and information received from the spectroscopy module 210 to obtain various spectral plots and images, and to also carry out various multivariate image analysis methods discussed herein.

Figure 3A:
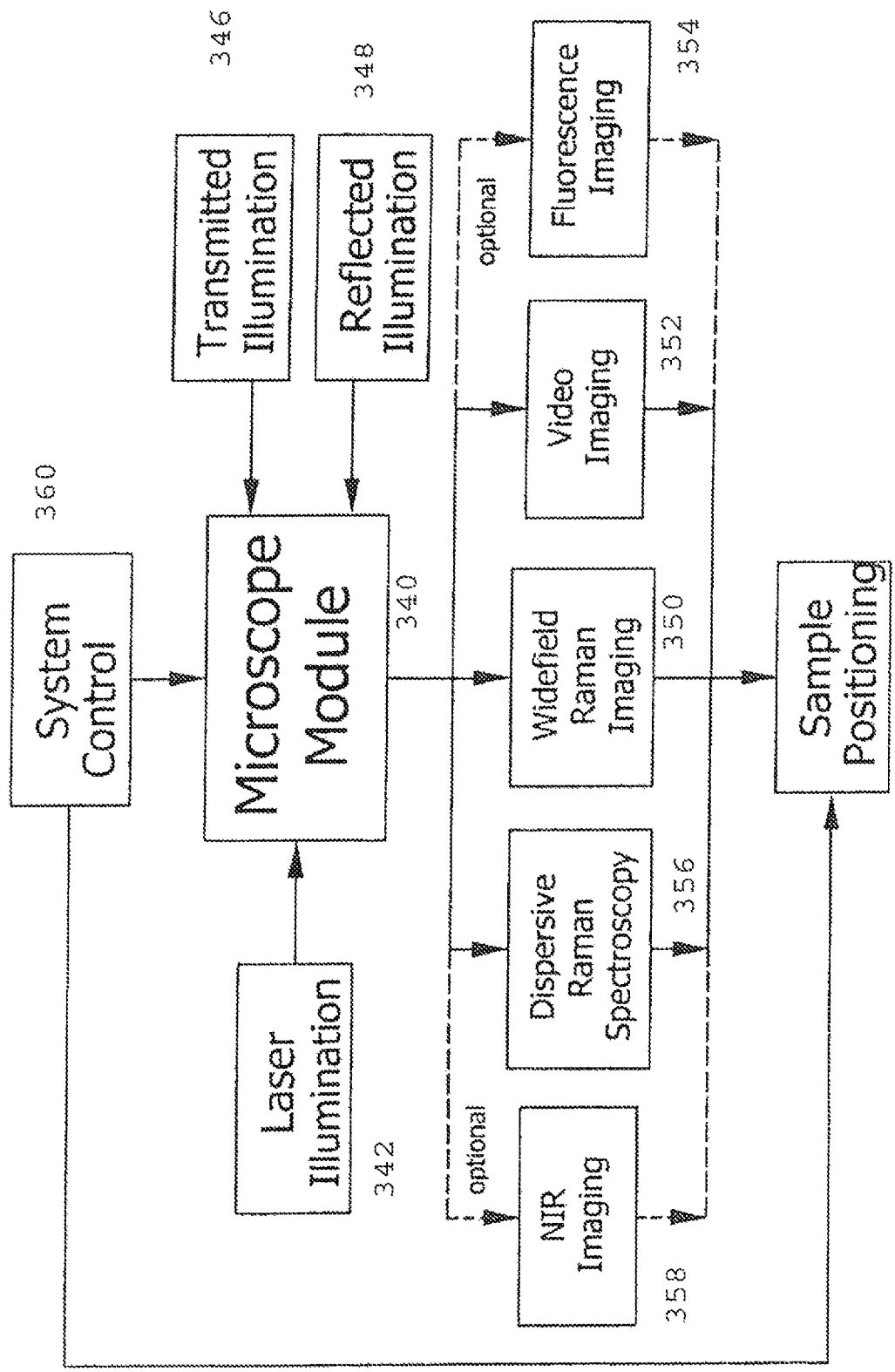
FIGS. 3A and 3B are representative of systems of the present disclosure.

FIG. 3A illustrates an exemplary schematic layout of the spectroscopy module 210 shown in FIG. 2. The layout in FIG. 3A may relate to the Falcon II™ Raman chemical imaging system marketed by ChemImage Corporation of Pittsburgh, Pa. In one embodiment, the . spectroscopy module 210 may include a microscope module 340 containing optics for microscope applications. An illumination source 342 (e.g., a laser illumination source) may provide illuminating photons to a sample (not shown) handled by a sample positioning unit 344 via the microscope module 340. In one embodiment, photons transmitted, reflected, emitted, or scattered from the illuminated sample (not shown) may pass through the microscope module (as illustrated by exemplary blocks 346, 348 in FIG. 3A) before being directed to one or more of spectroscopy or imaging optics in the spectroscopy module 210. In the embodiment of FIG. 3A, dispersive Raman spectroscopy 356, widefield Raman imaging 350, and brightfield video imaging 352 are illustrated as "standard" operational modes of the spectroscopy module 210. Two optional imaging modes—fluorescence imaging 354 and NIR (Near Infrared) imaging 358—may also be provided if desired. The spectroscopy module 210 may also include a control unit 360 to control operational aspects (e.g., focusing, sample placement, laser beam transmission, etc.) of various system components including, for example, the microscope module 340 and the sample positioning unit 344 as illustrated in FIG. 3A. In one embodiment, operation of various components (including the control unit 360) in the spectroscopy module 210 may be fully automated or partially automated, under user control.

It is noted here that in the discussion herein the terms "illumination," "illuminating," "irradiation," and "excitation" are used interchangeably as can be evident from the context. For example, the terms "illumination source," "light source," and "excitation source" are used interchangeably. Similarly, the terms "illuminating photons" and "excitation photons" are also used interchangeably. Furthermore, although the discussion herein below focuses more on Raman spectroscopy and Raman molecular imaging, various methodologies discussed herein may be adapted to be used in conjunction with other types of spectroscopy applications as can be evident to one skilled in the art based on the discussion provided herein.

Figure 3B:
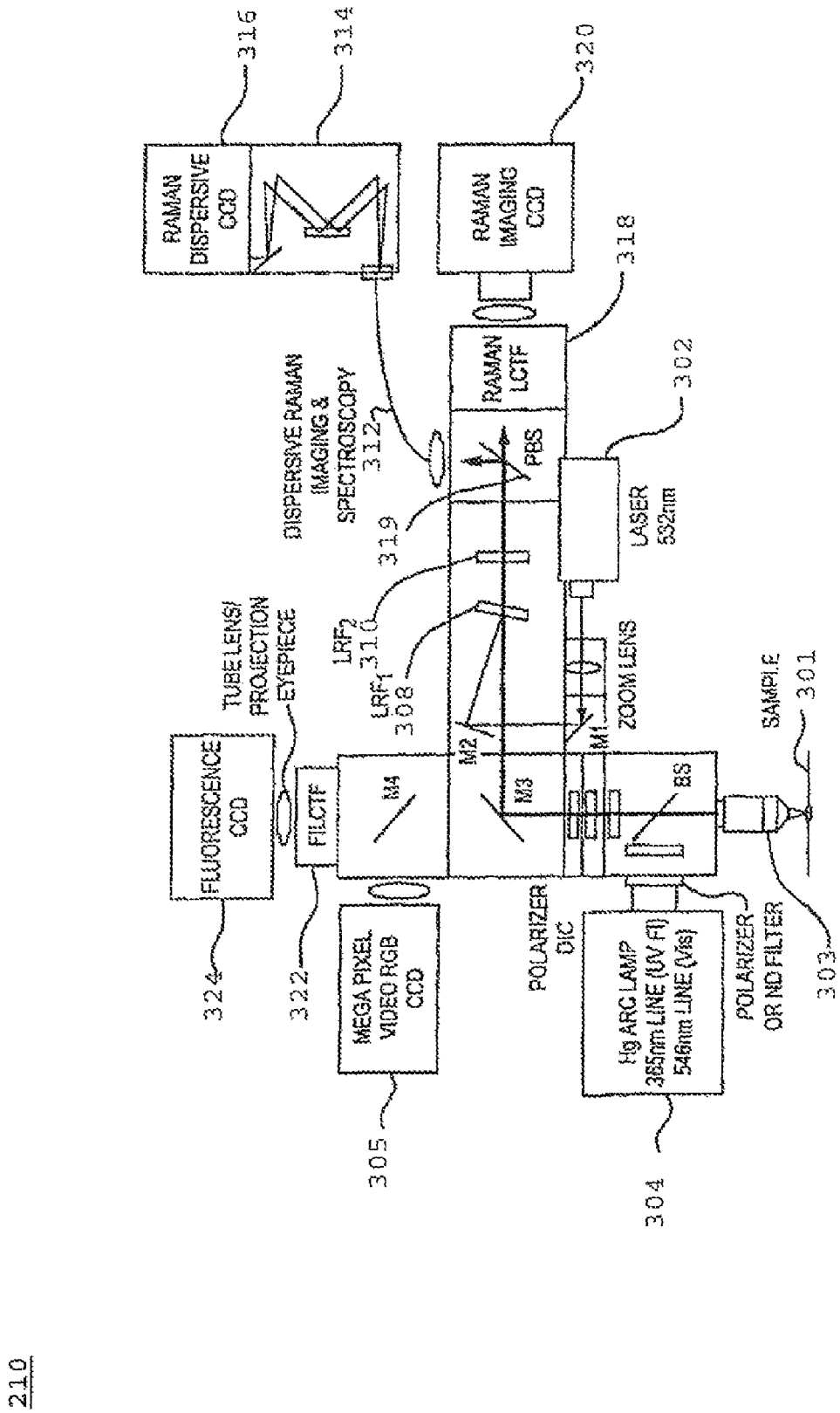

FIG. 3B illustrates exemplary details of the spectroscopy module 210 in FIG. 3A according to one embodiment of the present disclosure. Spectroscopy module 210 may operate in several experimental modes of operation including bright field reflectance and transmission imaging, polarized light imaging, differential interference contrast (DIC) imaging, UV induced autofluorescence imaging, NIR imaging, wide field illumination whole field Raman spectroscopy, wide field spectral fluorescence imaging, and wide field spectral Raman imaging. Module 210 may include collection optics 303, light sources 302 and 304, and a plurality of spectral information processing devices including, for example: a tunable fluorescence filter 322, a tunable Raman filter 318, a dispersive spectrometer 314, a plurality of detectors including a fluorescence detector 324, and Raman detectors 316 and 320, a fiber array spectral translator ("FAST") device 312, filters 308 and 310, and a polarized beam splitter (PBS) 319. In one embodiment, the processor 222 (FIG. 2) may be operatively coupled to light sources 302 and 304, and the plurality of spectral information processing devices 314, 318 and 322. In another embodiment, the processor 222 (FIG. 2), when suitably programmed, can configure various functional parts of the spectroscopy module in FIG. 2 and may also control their operation at run time. The processor, when suitably programmed, may also facilitate various remote data transfer and analysis operations discussed in conjunction with FIG. 4. Module 210 may optionally include a video camera 305 for video imaging applications. Although not shown in FIG. 3B, spectroscopy module 210 may include many additional optical and electrical components to carry out various spectroscopy and imaging applications supported thereby.

A fiber array spectral translator ("FAST") system when used in conjunction with a photon detector allows massively parallel acquisition of full-spectral images. A FAST system can provide rapid real-time analysis for quick detection, classification, identification, and visualization of the sample. The FAST technology can acquire a few to thousands of full spectral range, spatially resolved spectra simultaneously. A typical FAST array contains multiple optical fibers that may be arranged in a two-dimensional array on one end and a one dimensional (i.e., linear) array on the other end. The linear array is useful for interfacing with a photon detector, such as a charge-coupled device ("CCD"). The two-dimensional array end of the FAST is typically positioned to receive photons from a sample. The photons from the sample may be, for example, emitted by the sample, reflected off of the sample, refracted by the sample, fluoresce from the sample, or scattered by the sample. The scattered photons may be Raman photons.

In a FAST spectrographic system, photons incident to the two-dimensional end of the FAST may be focused so that a spectroscopic image of the sample is conveyed onto the two-dimensional array of optical fibers. The two-dimensional array of optical fibers may be drawn into a one-dimensional distal array with, for example, serpentine ordering. The one-dimensional fiber stack may be operatively coupled to an imaging spectrograph of a photon detector, such as a charge-coupled device so as to apply the photons received at the two-dimensional end of the FAST to the detector rows of the photon detector.

One advantage of this type of apparatus over other spectroscopic apparatus is speed of analysis. A complete spectroscopic imaging data set can be acquired in the amount of time it takes to generate a single spectrum from a given material. Additionally, the FAST can be implemented with multiple detectors. The FAST system allows for massively parallel acquisition of full-spectral images. A FAST fiber bundle may feed optical information from its two-dimensional non-linear imaging end (which can be in any non-linear configuration, e.g., circular, square, rectangular, etc.) to its one-dimensional linear distal end input into the photon detector.

Referring again to FIG. 3B, light source 302 may be used to irradiate the sample 301 with substantially monochromatic light. Light source 302 can include any conventional photon source, including, for example, a laser, an LED (light emitting diode), or other IR (infrared) or near IR (NIR) devices. The substantially monochromatic radiation reaching sample 301 illuminates the sample 301, and may produce photons scattered from different locations on or within the illuminated sample 301. A portion of the Raman scattered photons from the sample 301 may be collected by the collection optics 303 and directed to dispersive spectrometer 314 or Raman tunable filter 318 for further processing discussed later herein below. In one embodiment, light source 302 includes a laser light source producing light at 532.1 nm. The laser excitation signal is focused on the sample 301 through combined operation of reflecting mirrors M1, M2, M3, the filter 308, and the collection optics 303 as illustrated by an exemplary optical path in the embodiment of FIG. 3B. The filter 308 may be tilted at a specific angle from the vertical (e.g., at 6.5°) to reflect laser illumination onto the mirror M3, but not to reflect Raman-scattered photons received from the sample 301. The other filter 310 may not be tilted (i.e., it remains at 0° from the vertical). Filters 308 and 310 may function as laser line rejection filters to reject light at the wavelength of laser light source 302.

In the spectroscopy module 210 in the embodiment of FIG. 3B, the second light source 304 may be used to irradiate the sample 301 with ultraviolet light or visible light. In one embodiment, the light source 304 includes a mercury arc (Hg arc) lamp that produces ultraviolet radiation (UV) having wavelength at 365 nm for fluorescence spectroscopy applications. In yet another embodiment, the light source 304 may produce visible light at 546 nm for visible light imaging applications. A polarizer or neutral density (ND) filter with or without a beam splitter (BS) may be provided in front of the light source 304 to obtain desired illumination light intensity and polarization.

In the embodiment of FIG. 3B, the dispersive spectrometer 314 and the Raman tunable-filter 318 function to produce Raman data sets of sample 301. A Raman data set corresponds to one or more of the following: a of Raman spectra of the sample: and a of spatially accurate wavelength resolved Raman image of the sample. The Raman spectra and/or Raman images may be collected over a range of Raman shift values. In one embodiment, a Raman spectrum and/or Raman image may be collected at a plurality of Raman shift values ranging from 500 $cm^{-1}$ to 3200 $cm^{-1}$. In another embodiment, a Raman spectrum and/or Raman image may be collected at a plurality of Raman shift values ranging from 400 $cm^{-1}$ to 1850 $cm^{-1}$.

A sample 301 may be placed at a focusing location (e.g., by using the sample positioning unit 344 in FIG. 3A) to receive illuminating photons and to also provide reflected, emitted, scattered, or transmitted photons from the unknown sample 301 to the collection optics 303. The unknown sample 301 may include a variety of biological samples including but not limited to cells, tissues, and organs. In one embodiment, the unknown sample 301 includes at least one cell. In another embodiment, the unknown sample comprises at least one tissue containing a plurality of cells. The unknown sample may contain normal (non-diseased or benign) cells, diseased cells (e.g., a state of acute rejection, a state of chronic rejection, a state of incipient rejection, etc.) or a combination of normal and diseased cells.

Figure 4:
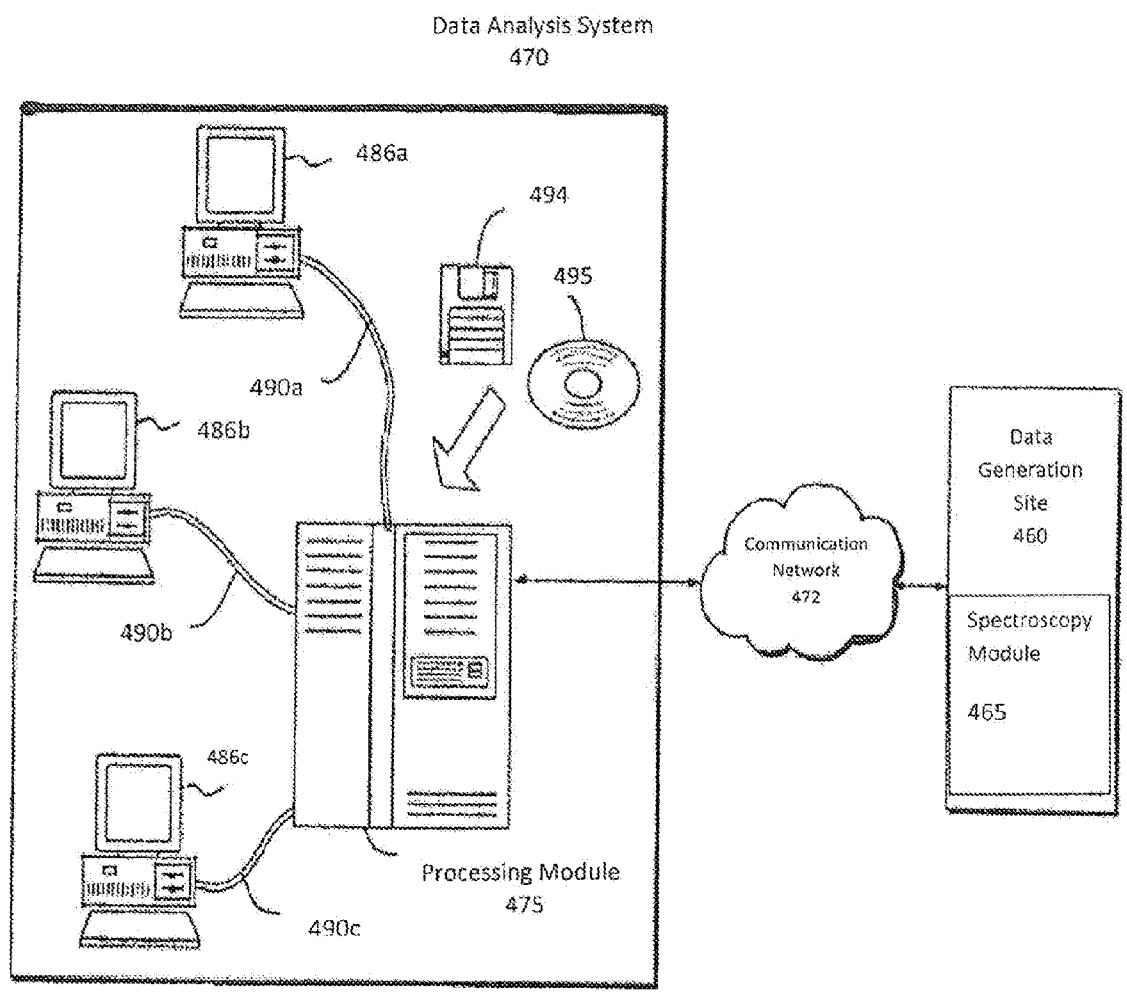
FIG. 4 is illustrative of a system of the present disclosure.

FIG. 4 depicts an exemplary setup to remotely perform spectroscopic analysis of test samples according to one embodiment of the present disclosure. Spectroscopic data from a test sample may be collected at a data generation site 460 using a spectroscopy module 465. In one embodiment, the spectroscopy module may be functionally similar to the spectroscopy module 210 discussed hereinbefore with reference to FIGS. 3A-3B. The spectroscopic data collected at the data generation site 460 may be transferred to a data analysis site 470 via a communication network 472. In one embodiment, the communication network 472 may be any data communication network such as an Ethernet LAN (local area network) connecting all the data processing and computing units within a facility, e.g., a university research laboratory, or a corporate research center. In that case, the data generation site 460 and the data analysis site 470 may be physically located within the same facility, e.g., a university research laboratory or a corporate research center. In alternative embodiments, the communication network 472 may include, independently or in combination, any of the present or future wireline or wireless data communication networks such as, for example, the Internet, the PSTN (public switched telephone network), a cellular telephone network, a WAN (wide area network), a satellite-based communication link, a MAN (metropolitan area network), etc. In some embodiments, the data generation site 460 and the data analysis site 470 that are linked by the communication network 472 may be owned or operated by different entities.

The data analysis site 470 may include a processing module 475 to process the spectroscopic data received from the data generation site 460. In one embodiment, the processing module 475 may be similar to the processing module 220 and may also include a number of different databases (not shown) storing different reference spectroscopic data sets. The processing module 475 may include a processor (similar to the processor 222 of the processing module 220 in FIG. 2) that is configured to execute program code or software to perform various spectral data processing tasks according to the teachings of the present disclosure. The machine-readable program code containing executable program instructions may be initially stored on a portable data storage medium, e.g., a floppy diskette 494, a compact disc or a DVD 495, a data cartridge tape (not shown), or any other suitable digital data storage medium. The processing module 475 may include appropriate disk drives to receive the portable data storage medium and may be configured to read the program code stored thereon, thereby facilitating execution of the program code by its processor. The program code, upon execution by the processor of the processing module 475, may cause the processor to perform a variety of data processing and display tasks including, for example, initiate transfer of spectral data set from the data generation site 460 to the data analysis site 470 via the communication network 472, compare the received spectral data set to various reference data sets stored in the databases of the processing module 475, classify or identify the test sample based on the comparison (e.g., disease state and/or clinical outcome), transfer the classification or identification results to the data generation site 460 via the communication network 472, etc.

In one embodiment, the data analysis site 470 may include one or more computer terminals 486A-486C communicatively connected to the processing module 475 via corresponding data communication links 490A-490C, which can be serial, parallel, or wireless communication links, or a suitable combination thereof. Thus, users may utilize functionalities of the processing module 475 via their computer terminals 486A-486C, which may also be used to display spectroscopic data received from the data generation site 460 and the results of the spectroscopic data processing by the processing module 475, among other applications. It is evident that in a practical application, there may be many more computer terminals 486 than just three terminals shown.

The computer terminals 486A-486C may be, e.g., a personal computer (PC), a graphics workstation, a multiprocessor computer system, a distributed network of computers, or a computer chip embedded as part of a machine or mechanism. Similarly, the data generation site 460 may include one or more of such computers (not shown) for viewing the results of the spectroscopic analysis received from the data analysis site 470. Each computer terminal, whether at the data generation site 460 or at the data analysis site 470, may include requisite data storage capability in the form of one or more volatile and non-volatile memory modules. The memory modules may include RAM (random access memory), ROM (read only memory) and HDD (hard disk drive) storage.

It is noted that the arrangement depicted may be used to provide a commercial, network-based spectroscopic data processing service that may perform customer-requested processing of spectroscopic data in real time or near real time. For example, the processing module 475 at the data analysis site 470 may be configured to identify a test sample from the spectroscopic data remotely submitted to it over the communication network 472 (e.g., the Internet) from the spectroscopy module 465 automatically or through an operator at the data generation site 460. The client or physician site (data generation site) 460 may be, for example, a government laboratory, a medical facility (doctor's office, hospital) or laboratory, including a pathology laboratory. The results of spectroscopic data analysis may be transmitted back to the client site 460 for review and further analysis. In one embodiment, the whole data submission, analysis, and reporting process can be automated.

It is further noted that the owner or operator of the data analysis site 470 may commercially offer a network-based spectroscopic data content analysis service, as illustrated by the arrangement, to various individuals, corporations, governmental entities, laboratories, or other facilities on a fixed-fee basis, on a per-operation basis or on any other payment plan mutually convenient to the service provider and the service recipient.

Figure 5:
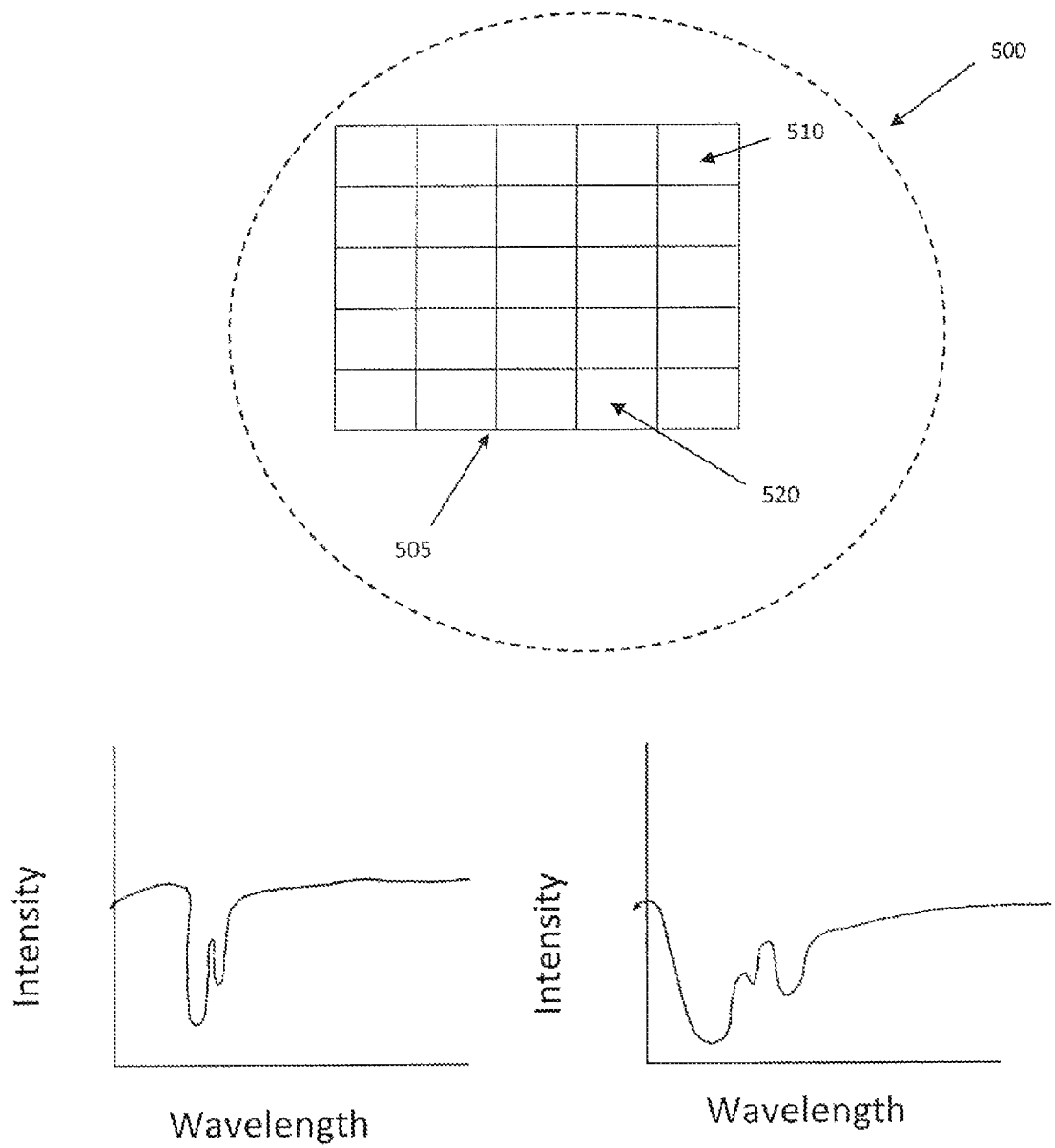
FIG. 5 is illustrative of one embodiment of the present disclosure wherein a test Raman data set is associated with a region of interest of the sample.

In still another embodiment, represented by FIG. 5, the test Raman data set is associated with a region of interest of the sample 500. The test Raman data set contains a plurality of test Raman spectra. The associated region of interest 505 is defined by a plurality of x and y spatial coordinates, 510 and 520. Each x,y spatial coordinate 510, 520 has an associated test Raman spectrum 540 and 550, respectively. In one such embodiment, the region of interest contains at least one of the following: an epithelium area, a stroma area, epithelial-stromal junction (ESJ) area, nuclei area, tissue area of interest, organ area of interest, extracellular material, cellular material, among other constituent material that may be found in a tissue or organ sample under investigation related to transplant procedures (screening, testing, determination of disease state or clinical outcome).

Any chemometric technique known in the art may be used in conjunction with the systems and methods described herein. Such chemometric techniques may include but are not limited to: spectral mixture resolution. Principle Component Analysis (PCA), minimum noise fraction, linear discriminate analysis, Mahalanobis distance, partial least squares discriminate analysis, Euclidean distance, partial least squares regression, support vector machines, maximum likelihood estimation, Bayesian classification, neutral networks, hidden markov models, and k-nearest neighbors, among others.

In spectral mixture resolution, a test spectrum is approximated with a linear combination of reference spectra with a goal of minimizing the deviation of the approximation from the test spectrum. The process results in a set of relative weights for the reference spectra.

In Principle Component Analysis, the analysis results in a set of mathematical vectors defined based on established methods used in multivariate analysis. The vectors form an orthogonal basis, meaning that they are linearly independent vectors and can be used as a classification model as described herein. The vectors are determined based on a set of input data by first choosing a vector which describes the most variance within the input data. This first "principle component", or PC, is subtracted from each of the members of the input set. The input set after this subtraction is then evaluated in the same fashion (a vector describing the most variance in this set is determined and subtracted) to yield a second vector—the second principle component. The process is iterated until either a chosen number of linearly independent vectors (PCs) are determined, or a chosen amount of the variance within the input data is accounted for.

In one embodiment, the Principal Component Analysis based classification may include a series of steps. A predetermined vector space, alternatively described as a "classification model", is selected that mathematically describes a plurality of reference Raman data sets. The test Raman data set may be transformed into the pre-determined vector space, and then a distribution of transformed data may be analyzed in the pre-determined vector space.

The analysis of the distribution of the transformed data may be performed using a number of classification schemes. Some examples of the classification scheme may include: Mahalanobis distance, Adaptive subspace detector, Band target entropy method, Neural network, and support vector machine, among others known to those skilled in the art.

In one such embodiment, the classification scheme is Mahalanobis distance. The Mahalanobis distance is an established measure of the distance between two sets of points in a multidimensional space that takes into account both the distance between the centers of two groups, but also the spread around each centroid. A Mahalanobis distance model of the data is represented by plots of the distribution of the spectra in the principal component space. The Mahalanobis distance calculation is a general approach to calculating the distance between a single point and a group of points. It is useful because rather than taking the simple distance between the single point and the mean of the group of points, Mahalanobis distance takes into account the distribution of the points in space as part of the distance calculation. The Mahalanobis distance is calculated using the distances between the points in all dimensions of the principal component space.

In one such embodiment, once the test Raman data set is transformed into the space defined by the predetermined PC vector space, the test Raman data set is analyzed relative to the predetermined vector space. This may be performed by calculating a Mahalanobis distance between the test Raman data set transformed into said vector space and the reference Raman data sets in said pre-determined vector space.

In another embodiment the test Raman dataset is used in conjunction with a partial least squares linear discriminate analysis to achieve a classification in terms of rejection or not rejection. In another embodiment the results of a classification based on the Raman data set using any of a number of methods including, but not limited to spectral mixture resolution, Euclidian distance, Mahalanobis distance and partial least squares linear discriminate analysis are generated and subsequently combined with results from a separate classification of either a characteristic of the Raman data set, or of a second data set acquired on the sample. Examples of second data sets which can be acquired on the tissue sample are polarized light microscopy, bright field light microscopy, spectral fluorescence imaging, integrated intensity fluorescence imaging. The second dataset can be classified using the methods above leading to a second set of results. The first results from the Raman data and the second results from the second data can be scaled appropriately and combined to render a final result for the tissue which was sampled.

In one embodiment of the present disclosure, the systems and methods described herein can also be used to classify the clinical outcome in a patient in addition to the disease slate. After organ or tissue transplantation, the host may begin to reject the transplanted material. After rejection begins, there is the possibility that the rejection will lead to organ or tissue failure. However, if rejection is recognized, drug therapies or other approaches may be used to stop the course of rejection. For example, steroids can be used to suppress the patient's immune system and therefore prevent the body from attacking (rejecting) the transplanted material. If an intervening approach is successful in stopping the course of rejection, the clinical outcome may be organ or tissue function as opposed to failure. For example, if the systems and methods described herein are employed and a biological tissue sample is identified as being in a state of incipient rejection, intervening measures can be used to stop or slow the course of rejection and thereby prevent organ failure in the patient. Therefore, it would be advantageous to be able to detect rejection (disease state) in an organ or tissue that has been or will be transplanted to be able to intervene early enough to prevent failure of the organ or tissue. It is also advantageous to be able to detect a clinical outcome of failure so that the organ or tissue can be removed or other measures be taken. Likewise, being able to detect a clinical outcome of organ or tissue function is equally important to assessing a patient's condition and determining whether or not other treatments are needed.

In addition to tissue or organ failure or function, clinical outcome can also be used to characterize a progressive or a non-progressive disease. In one embodiment, a progressive stale can be a state where the organ will develop failure defined by clinical measures of function in either a chronic or acute progression pattern. The determination of progressive vs. non-progressive can also be extended to describe other types of disease or metabolic states. For example, diabetes can be clinically described as "stable" or "well managed" by a clinician and would fall into the non-progressive class. In contrast, diabetes can be progressing though the common course of the disease with all the effects on kidneys, nerves, skin, heart, and other organs, which is part of the disease. As a second example, multiple sclerosis is a disease which exists in many people in a stable, non-progressive state. In others, the disease rapidly progresses through historically observed patterns of physical characteristics with clinical manifestations.

In one embodiment of the present disclosure, a reference data base is provided wherein the reference data base comprises a plurality of reference spectral data sets. The plurality of reference spectra data sets may include but are not limited to: a plurality of reference Raman spectra, a plurality of reference spatially accurate wavelength resolved Raman images, a plurality of reference infrared spectra, a plurality of reference spatially accurate wavelength resolved infrared images, a plurality of reference near infrared spectra, a plurality of reference spatially accurate wavelength resolved near infrared images, a plurality of reference mid infrared spectra. a plurality of reference spatially accurate wavelength resolved mid infrared images, a plurality of reference ultraviolet spectra, a plurality of reference spatially accurate wavelength resolved ultraviolet images, a plurality of reference fluorescence spectra, a plurality of reference spatially accurate wavelength resolved fluorescence images, a plurality of reference visible spectra, a plurality of reference spatially accurate wavelength resolved visible images, and combinations thereof, among others. The plurality of reference spectral data sets may each correspond to a known material (e.g., tissue, cell, organ, etc.). The reference spectral data sets may also each correspond to a known disease state (e.g., no disease state, state of acute rejection, state of chronic rejection, state of incipient rejection, etc.) and/or a known clinical outcome (organ failure or organ function).

Therefore, in addition to Raman spectroscopic methods, the systems and methods of the present disclosure contemplate the use of other spectroscopic techniques to determine disease state and/or clinical outcome of a sample, including but not limited to: infrared, near infrared, mid infrared, ultraviolet, fluorescence, visible spectroscopy, and combinations thereof, among others. It is also contemplated by the present disclosure that in one embodiment, such spectroscopic techniques can be combined with a visible microscopic image to thereby evaluate the morphology, morophometry, histology and other attributes of a sample of interest.

Figure 6:
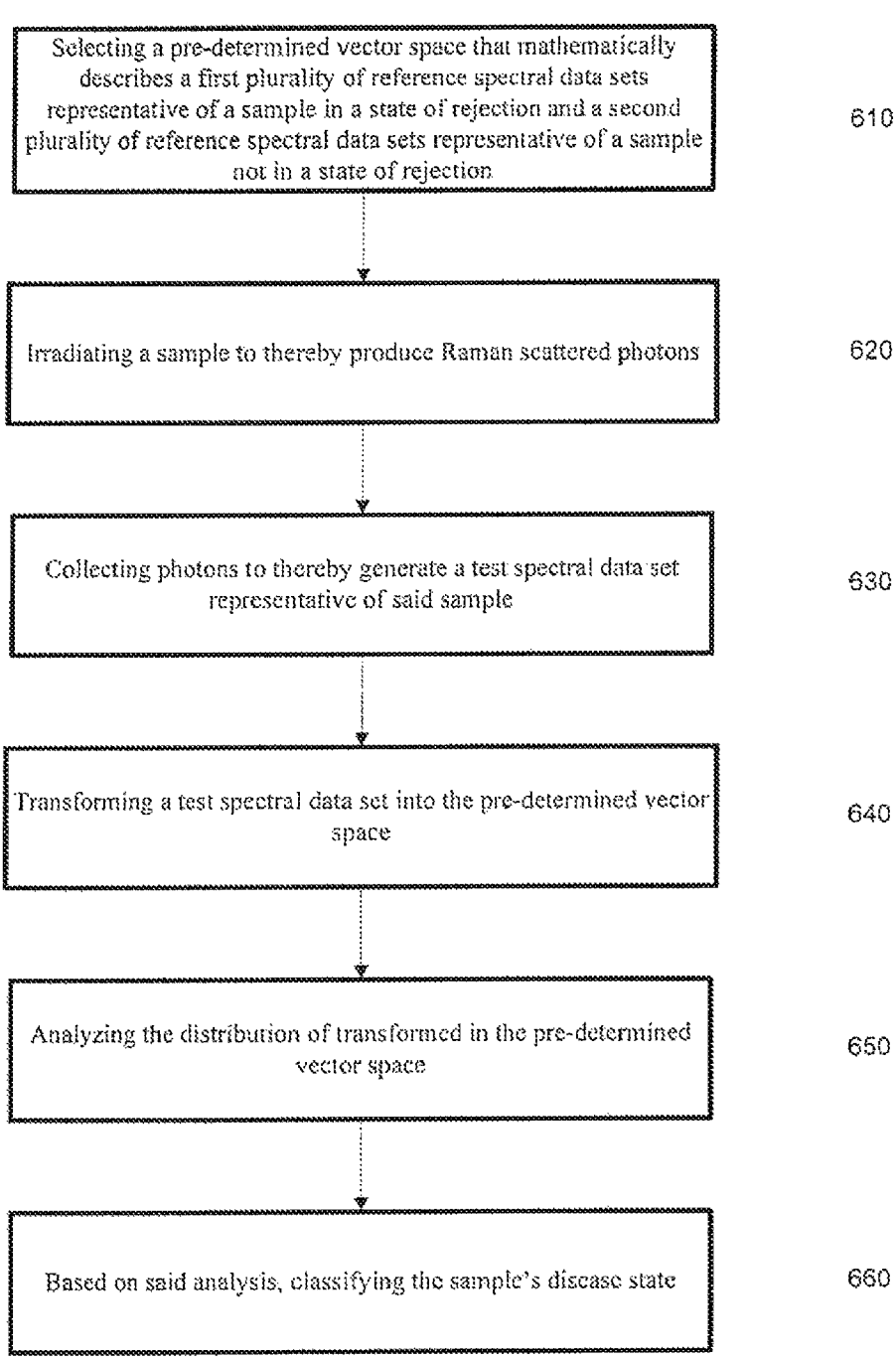
FIG. 6 is illustrative of one method of the present disclosure.

FIG. 6 illustrates another method of the present disclosure which uses Principle Component Analysis. The method 600 provides for selecting a pre-determined vector space that mathematically describes a first plurality of reference spectral data sets representative of a sample in a state of rejection and a second plurality of reference spectral data sets representative of a sample not in a state of rejection in step 610. In step 620, a sample is irradiated to thereby produce Raman scattered photons. In one embodiment, the sample comprises a biological tissue. In step 630, the photons are collected to thereby generate a test spectral data set representative of said sample. The test spectral data set is transformed into the pre-determined vector space in step 640. In step 650, the distribution of transformed in the pre-determined vector space is analyzed. Based on said analysis, the sample's disease state can be classified in step 660. The disease state may include but is not limited to: no state of rejection, a state of acute rejection, a state of chronic rejection, and a state of incipient rejection.

Figure 7:
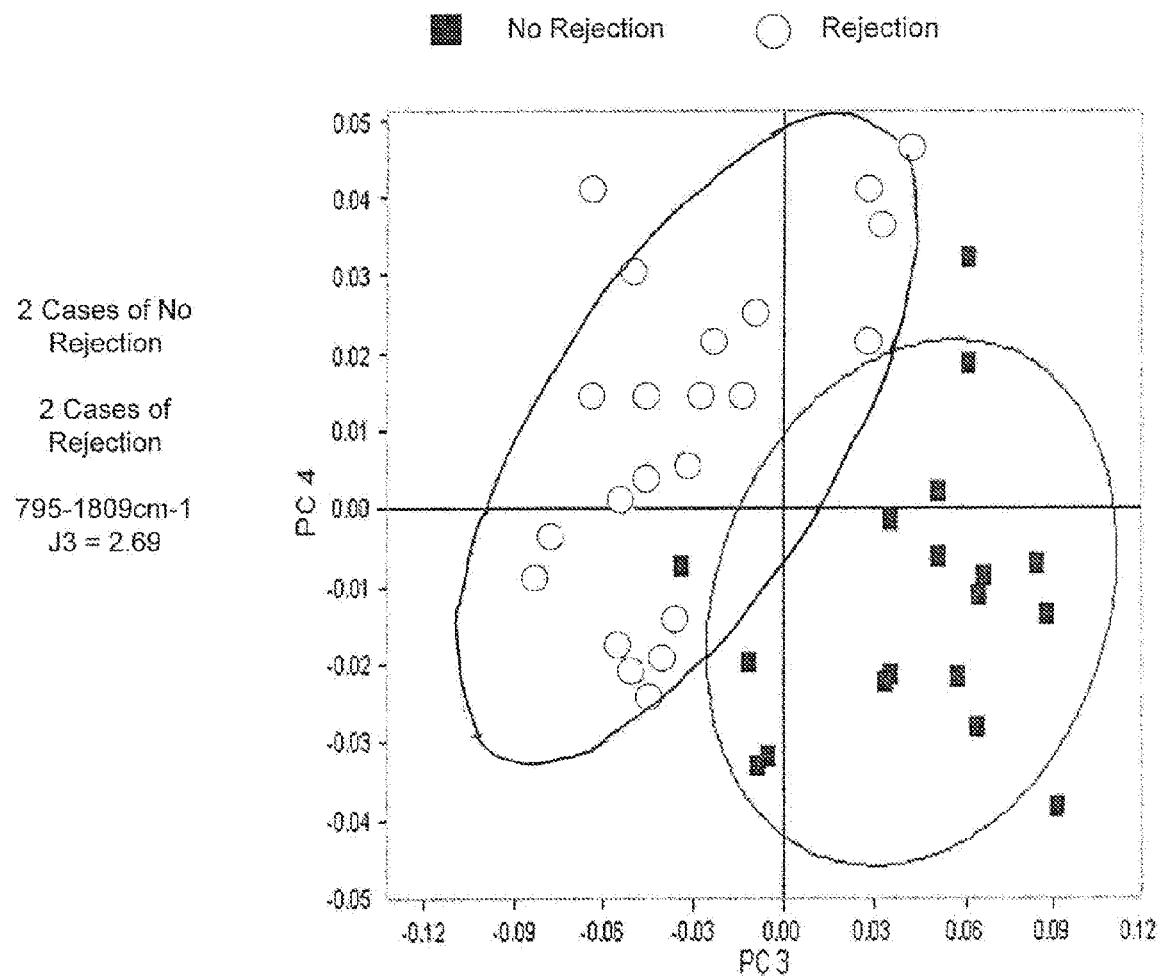
FIG. 7 is a scatter plot of measurements of Raman scattered light from two samples of kidney tissue undergoing rejection and two samples of kidney tissue not undergoing rejection.

FIG. 7 shows a scatter plot of measurements of Raman scattered light from two samples of kidney tissue undergoing rejection and two samples of kidney tissue not undergoing rejection. Individual measurements are represented by points in the Figure. The circular points represent measurements made on samples which are undergoing rejection. The square points represent measurements made on samples which are not undergoing rejection. The scatter plot is the result of Principle Component Analysis of the data and show, in the orthogonal vector space defined by the principle component vectors, the location of the data points relative to one another. The fact that points representative of the samples that underwent rejection are separate and distinct from those points that did not undergo rejection is indicative that the use of Principle Component Analysis in analyzing Raman scattering measurements holds potential for distinguishing tissues undergoing rejection from those that are not.

Figure 8:
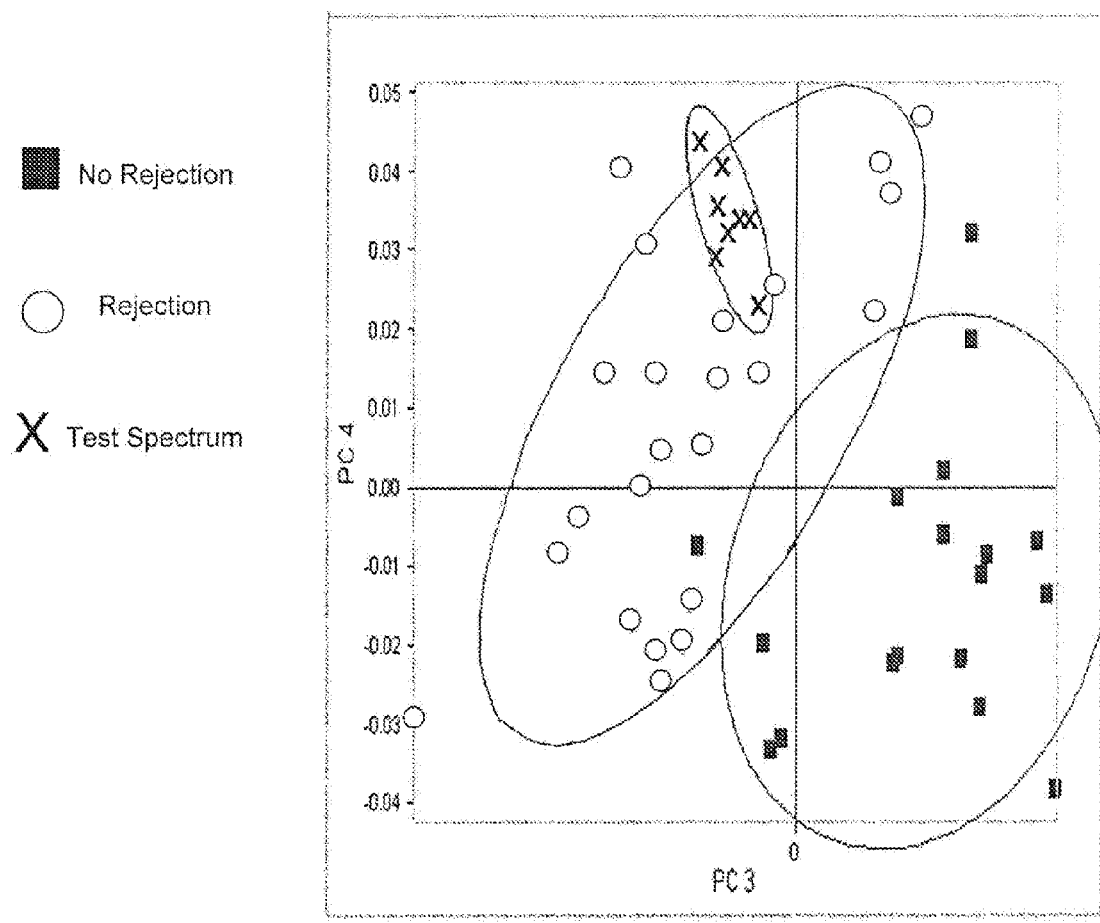
FIG. 8 is the same scatter plot as FIG. 7 with the addition of test data from a separate measurement of the Raman scattered light which has been transformed into the vector space defined by the principle components.

FIG. 8 shows the sample scatter plot as FIG. 7 with the addition of test data from a separate measurement of the Raman scattered light which has been transformed into the vector space defined by the principle components. The transformed data points are depicted as "x" symbols. In FIG. 7, the test data ("x" points) is clustered together within a region of circle points representative of samples taken from organs that went on to rejection. As a result, the test sample can be classified as a tissue that is also rejecting. The test spectra used in FIG. 8 were from a second region of interest in one model case. The region of interest was a glomerulus. The small cluster made by the glomeruli image spectra is evident.

Figure 9:
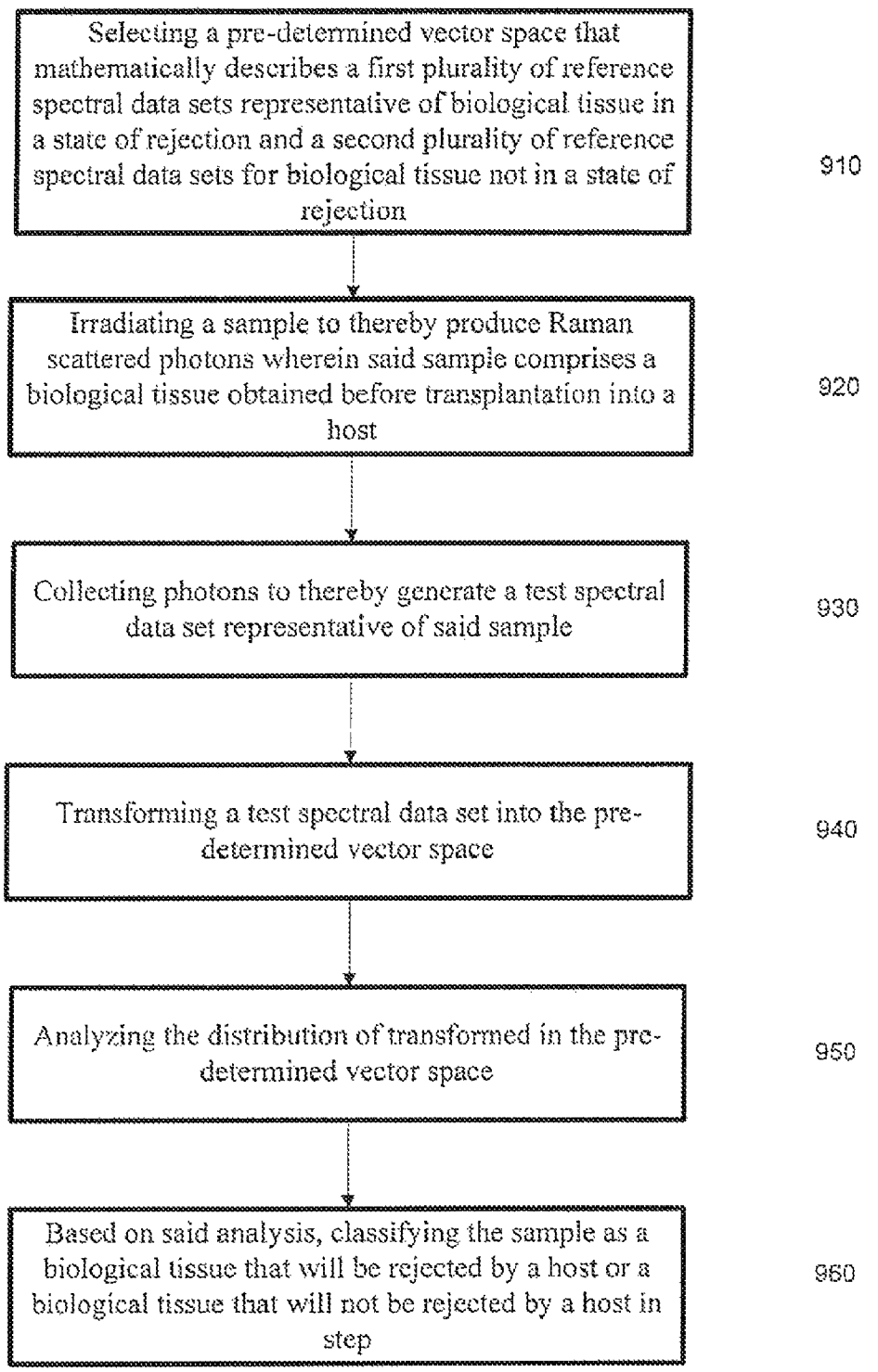
FIG. 9 is illustrative of one method of the present disclosure.

In another embodiment of the present disclosure, illustrated by FIG. 9, a sample is obtained from an organ prior to transplantation. The method 900 comprises selecting a pre-determined vector space that mathematically describes a first plurality of reference spectral data sets representative of biological tissue in a state of rejection and a second plurality of reference spectral data sets for biological tissue not in a state of rejection in step 910. In step 920 a sample is irradiated to thereby produce Raman scattered photons wherein said sample comprises a biological tissue obtained before transplantation into a host. In step 930 the photons are collected to thereby generate a test spectral data set representative of the sample. In step 940 the test spectral data set is transformed into the pre-determined vector space. The distribution of transformed data in the pre-determined vector space is analyzed in step 950. Based on said analysis, a sample can be classified as a biological tissue that will be rejected by a host or a biological tissue that will not be rejected by a host in step 960.

Figure 10:
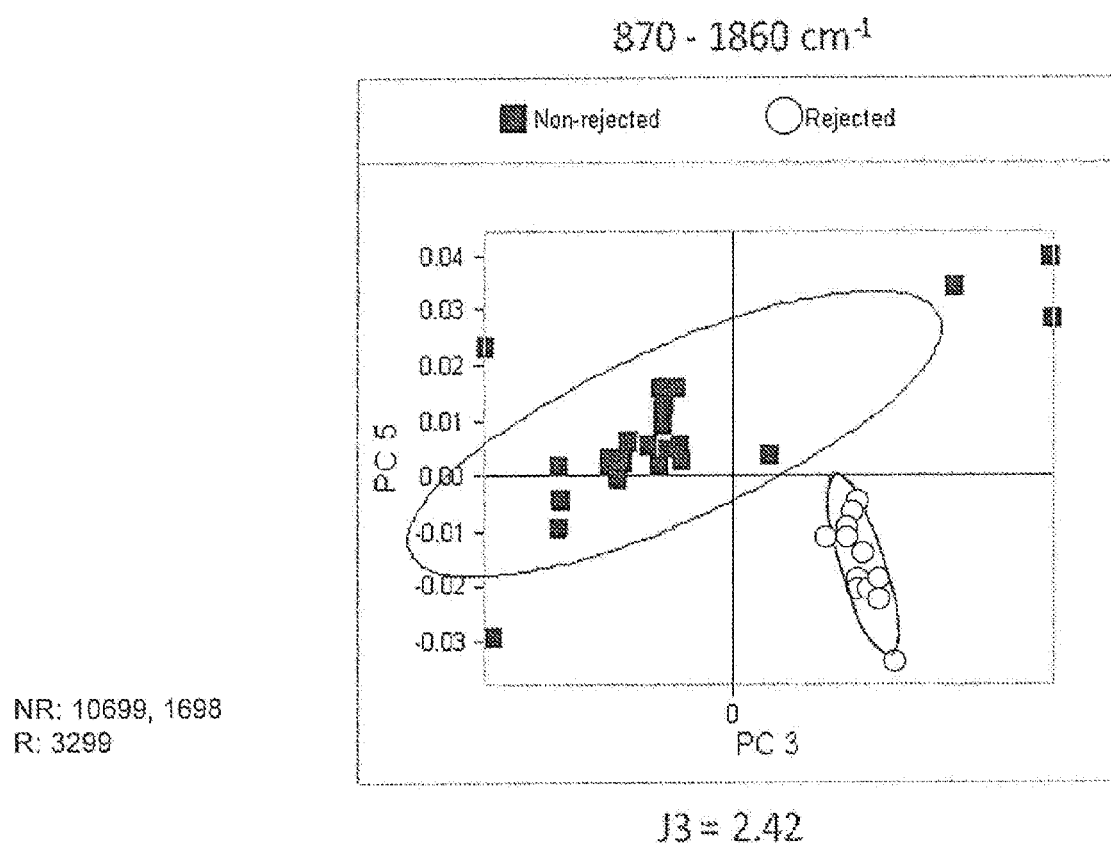
FIG. 10 is also a scatter plot produced as part of Principle Component Analysis of data based on Raman images of tissue samples wherein the samples are obtained prior to transplant.

FIG. 10 is also a scatter plot produced as part of Principle Component Analysis of data based on Raman images of tissue samples. In this case, the tissue samples are biopsy samples taken from organs prior to the transplant. As can be seen from the figure, some samples were taken from organs that went on to reject as other samples were taken from organs that did not go on to reject. The rejected and non-rejected points representative of the associated samples cue separate and distinct from each other. Such distribution is indicative of the potential this analysis holds for predicting whether or not a particular organ or tissue sample will undergo rejection at some later time.

The present disclosure may be embodied in other specific forms without departing from the spirit or essential attributes of the disclosure. Accordingly, reference should be made to the appended claims, rather than the foregoing specification, as indicating the scope of the disclosure. Although the foregoing description is directed to the preferred embodiments of the disclosure, it is noted that other variations and modification will be apparent to those skilled in the art, and may be made without departing from the spirit or scope of the disclosure.

What is claimed is:
1. A method comprising:
selecting a pre-determined vector space that mathematically describes a First plurality of reference spectral data sets representative of a biological tissue in a state of rejection and a second plurality of reference spectral data sets representative of a biological tissue not in a state of rejection;
irradiating a sample to thereby produce Raman scattered photons, wherein said sample comprises a biological tissue;
collecting said photons to thereby generate a test spectral data set representative of said sample;
transforming the test spectral data set into said pre-determined vector space;

analyzing a distribution of transformed data in the pre-determined vector space;

and based on said analysis, classifying the sample as at least one of: a biological tissue in no state of rejection, a biological tissue in a state of acute rejection, a biological tissue in a state of chronic rejection, and a biological tissue in a state of incipient rejection.

2. The method of claim 1 wherein said biological tissue comprises tissue associated with at least one of: kidney, heart, pancreas, prostate, lung, liver, blood, muscle, bladder, intestine, stomach, cornea, lens, bone, and skin.

3. The method of claim 1 further comprising determining a clinical outcome of a patient associated with said sample.

4. The method of claim 3 wherein said clinical outcome comprises at least one of: organ failure and organ function.

5. The method of claim 1 wherein said sample is obtained by a method selected from the group consisting of: fine needle aspiration, core biopsy, surgical biopsy, and combinations thereof.

6. The method of claim 1 wherein said first plurality of reference spectral data sets is further representative of a disease state that is selected from the group consisting of: a state of acute rejection, a state of chronic rejection, and a state of incipient rejection.

7. The method of claim 1 wherein said second plurality of reference spectral data sets is further representative of no disease state.

8. The method of claim 1 wherein said first plurality of reference spectral data sets comprises at least one of a plurality of reference Raman spectra and a plurality of reference spatially accurate wavelength resolved Raman images.

9. The method of claim 1 wherein said second plurality of reference spectral data sets comprises at least one of: a plurality of reference Raman spectra and a plurality of reference spatially accurate wavelength resolved Raman images.

10. A method comprising:
selecting a pre-determined vector space that mathematically describes a first plurality of reference spectral data sets representative of a biological tissue in a state of rejection and a second plurality of reference spectral data sets representative of a biological tissue not in a state of rejection;

irradiating a sample to thereby produce Raman scattered photons, wherein said sample comprises a biological tissue obtained before transplantation into a host;

collecting said photons to. thereby generate a test spectral data set representative of said sample;

transforming the test spectral data set into said pre-determined vector space;

analyzing a distribution of transformed data in the pre-determined vector space;

and based on said analysis, classifying the sample as at least one of: a biological tissue that will be rejected by a host and a biological tissue that will not be rejected by a host.

11. The method of claim 10 wherein said biological tissue, comprises tissue associated with at least one of: kidney, heart, pancreas, prostate, lung, liver, blood, muscle, bladder, intestine, stomach, cornea, lens, bone, and skin.

12. The method of claim 10 further comprising determining a clinical outcome of a patient associated with said sample.

13. The method of claim 12 wherein said clinical outcome comprises at least one of: organ failure and organ function.

14. The method of claim 10 wherein said sample is obtained by a method selected from the group consisting of: fine needle aspiration, core biopsy, surgical biopsy, and combinations thereof.

15. The method of claim 10 wherein said first plurality of reference spectral data sets is further representative of a disease state that is selected from the group consisting of: a state of acute rejection, a state of chronic rejection, and a state of incipient rejection.

16. The method of claim 10 wherein said second plurality of reference spectral data sets is further representative of no disease state.

17. The method of claim 10 wherein said first plurality of reference spectral data sets comprises at least one of: a plurality of reference Raman spectra and a plurality of reference spatially accurate wavelength resolved Raman images.

18. The method of claim 10 wherein said second plurality of reference spectral data sets comprises at least one of: a plurality of reference Raman spectra and a plurality of reference spatially accurate wavelength resolved Raman images.

* * * * *